US00PP36005P2

(12) United States Plant Patent
Clark

(10) Patent No.: US PP36,005 P2
(45) Date of Patent: Jul. 9, 2024

(54) ***COLEUS* PLANT NAMED 'UF20-103-6'**

(50) Latin Name: *Coleus scutellarioides*
Varietal Denomination: UF20-103-6

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,294

(22) Filed: Jun. 20, 2023

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469, 373
CPC ..... A01H 5/12; A01H 5/00; A01H 6/50
See application file for complete search history.

(56) References Cited

PUBLICATIONS

Ball Seed Solar Flare *Coleus* retrieved on Feb. 14, 2024 at https://www.ballseed.com/WEBTRACKPLANTINFO.ASPX?PHID=018009871010751&env=P, one page (Year: 2024).*

Tschanz Cloudy skies, cool temperatures are no match fo CAST 2023 retrieved from the Internet at https://mydigitalpublication.com/publication/?i=794147&article_id=4594513&view=articleBrowser, Jul. 2023, 6 pp. (Year: 2023).*

* cited by examiner

*Primary Examiner* — June Hwu

(74) *Attorney, Agent, or Firm* — Koenig IP Works, PLLC; Katherine Koenig

(57) ABSTRACT

A new and distinct cultivar of *Coleus* (*Coleus scutellarioides*) plant named 'UF20-103-6' having a combination of desirable traits that make it well-suited for use as an annual plant in the summer landscape. 'UF20-103-6' has consistent tri-color foliage patterning, compact growth habit, and moderate growth rate in the greenhouse and landscape. 'UF20-103-6' has ruffled, deeply lobed foliage with predominant centers colored purplish red surrounded by dark red sections, and consistent yellow green accents and leaf margins. 'UF20-103-6' maintains these contrasting colors and patterns in both sun and shade. 'UF20-103-6' is compact in habit, but it is highly branched and spreading in form, growing wider than it does tall.

3 Drawing Sheets

Genus and species: *Coleus scutellarioides*.
Cultivar denomination: 'UF20-103-6'.

CROSS-REFERENCE TO RELATED APPLCIATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF20-103-6'. The new cultivar 'UF20-103-6' originated from an open pollination conducted in May-November 2019 in Citra, Florida, between the female *Coleus* plant 'UF17-73-7' (unpatented) and an unknown male *Coleus* plant. A single seedling was chosen in May 2020 for further asexual propagation in Gainesville, Florida.

The new cultivar 'UF20-103-6' has been reproduced asexually for over 18 months through vegetative meristem tip cuttings and has been found to retain its distinctive characteristics through successive asexual propagations. 'UF20-103-6' was first propagated asexually by vegetative meristem tip cuttings in May 2020 in Gainesville, Florida, and has remained true-to-type since that time.

Plant Breeder's Rights for the new cultivar 'UF20-103-6' have not been applied for, and 'UF20-103-6' has not been made publicly available more than one year prior to the filing date of this application.

SUMMARY OF THE INVENTION

The new cultivar 'UF20-103-6' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'UF20-103-6' was selected for its consistent foliage color patterning, and also for its consistent growth rate and vigor in the greenhouse and landscape. 'UF20-103-6' has foliage that is consistently tri-colored, with purplish red centers surrounded by dark red sections and yellow green leaf margins. Normally this color combination changes in either full sun, where it is predominantly dark maroon with the loss of the distinctive yellow green leaf margins, or full shade, where the leaves display more magenta color and more color differentiation. 'UF20-103-6' is exceptional because it maintains its tri-color leaves consistently in both sun and shade. Vegetative cuttings from 'UF20-103-6' form roots in one week and consistently produce vivid pink color when grown in the greenhouse.

The following are the most outstanding and distinguishing characteristics of 'UF20-103-6' when grown under normal horticultural practices in Gainesville, Florida: (1) 'UF20-103-6' has the combination of compact habit and spreading growth form, excellent heat tolerance, and consistent tri-colored leaves that are significantly different than other *Coleus* plants; (2) it has superior stability in foliage color in both sun and shade conditions, and it has excellent lateral branching, making it suitable for propagators and producers; and (3) 'UF20-103-6' has been observed to have long-season performance in landscape trials in Gainesville, Florida.

When compared to the female parent 'UF17-73-7', the new cultivar 'UF20-103-6' has medium-sized, deeply lobed and ruffled leaves that are slightly longer than they are wide. The leaves are predominantly purplish red through the center, surrounded by dark red sections, with yellow green margins. In contrast, 'UF17-73-7' also has deeply lobed leaves with ruffled edges, but they are larger, and are twice as long as they are wide. Additionally, 'UF17-73-7' leaves are predominantly colored dark maroon with darker green margins, and small areas of magenta at the leaf base. 'UF20-103-6' has a compact habit with a spreading form that is well-branched, whereas 'UF17-73-7' is much more vigorous, and more upright with a less spreading form.

DESCRIPTION OF THE FIGURES

This new *Coleus* cultivar 'UF20-103-6' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar; and FIG. 3 shows a close-up view of the foliage of the new *Coleus* cultivar.

DETAILED BOTANICAL DESCRIPTION OF THE CULTIVAR

Figure 1:
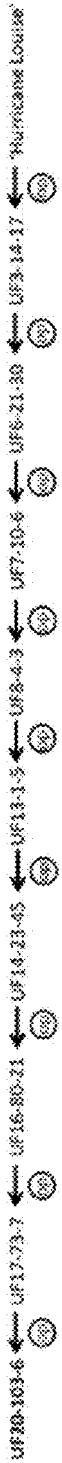
FIG. 1 shows the pedigree of the new *Coleus* cultivar 'UF20-103-6' as is shown and described herein.
Figure 2:
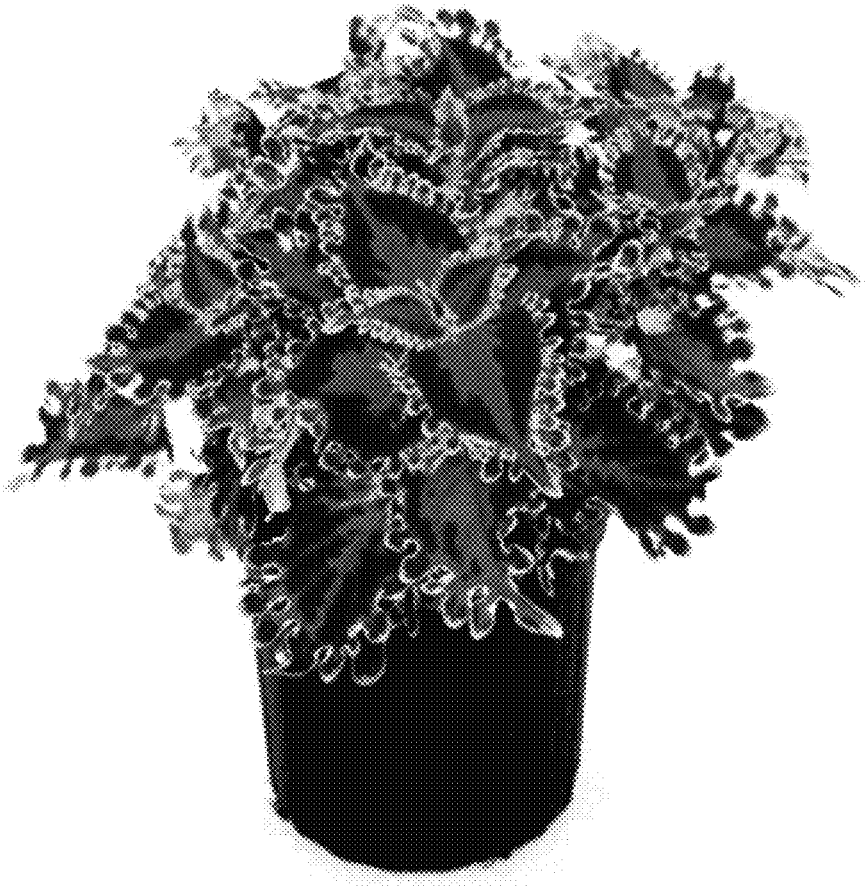
FIGS. 2 and 3 were taken from plants grown eleven weeks from unrooted cuttings in September-December 2022 in a glass-covered greenhouse in Gainesville, Florida.
Figure 3:
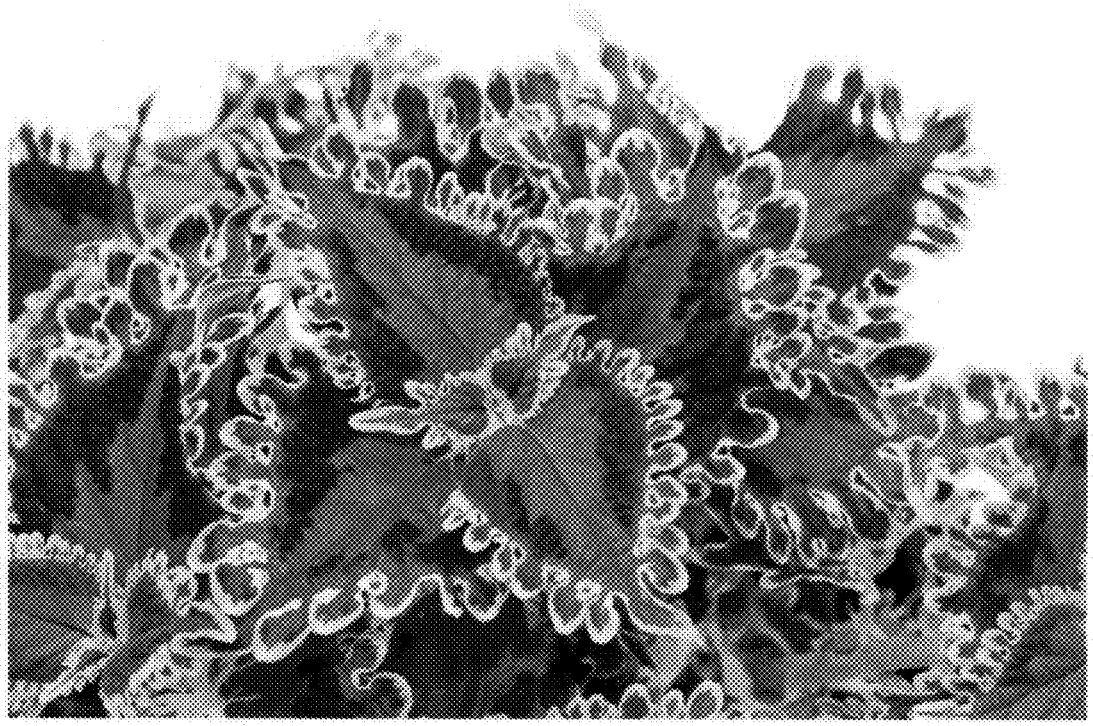

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color, but encompass hues, shades and tints, and color patterns differ from one genotype to another due to varying levels of variegation. The following detailed description of 'UF20-103-6' was obtained using eleven-week-old plants grown from unrooted cuttings in September-December 2022 in a glass-covered greenhouse in Gainesville, Florida. The plants were propagated in mist for ten days after cuttings were stuck, pinched, then grown in one-gallon pots for approximately nine and a half additional weeks.

Botanical Description

Botanical classification:

*Family*.—Lamiaceae.

*Botanical name*.—*Coleus scutellarioides*.

*Common name*.—*Coleus*.

*Cultivar name*.—'UF20-103-6'.

Parentage:

*Female or seed parent*.—'UF17-73-7'.

*Male or pollen parent*.—Unknown.

Plant description:

*Form*.—Spreading.

*Habit*.—Compact.

*Height* (*from top of soil*).—18-20 cm.

*Width* (*horizontal plant diameter*).—35-40 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2-3 days, roots initiate in 3-4 days and become a highly branched cutting in 7-10 days.

Branches:

*Quantity per plant*.—Approximately 7.

*Branch color*.—RHS 142B (yellow green).

*Texture*.—Smooth.

*Pubescence*.—Not present.

*Stem description*.—Square-shaped stem.

*Branch diameter*.—0.5-0.6 cm at the base of a 14-cm-long branch.

*Branch length*.—12-15 cm.

*Internode length*.—2.5-3.0 cm measured at mid-branch.

*Anthocyanin*.—Not present.

Leaves:

*Quantity of leaves per branch*.—14-16.

*Arrangement*.—Opposite.

*Fragrance*.—Not fragrant.

*Shape*.—Ovate.

*Length*.—9-10 cm.

*Width*.—7-8 cm.

*Apex*.—Broadly Acute.

*Base*.—Attenuate.

*Margin*.—Highly lobed.

*Lobes, depth of incision*.—About 1.0 cm to 1.5 cm.

*Leaf texture*.—Adaxial (top): Pulverulent. Abaxial (bottom): Smooth.

*Venation color*.—Upper surface: Apex: RHS N186B (dark greyish purple). Base: RHS 149D (yellow green). Lower surface: RHS 145C (yellow green).

*Venation pattern* (*both upper and lower surfaces*).—Reticulate.

*Color, immature leaf*.—Upper surface: Major color (center): RHS 60A (deep red). Secondary color (around center): RHS 187B (dark red). Margins: RHS 149A (yellow green). Base: RHS 149D (yellow green). Lobes (center): RHS 187B (dark red). Lobes (margin): RHS 149A (yellow green). Lower surface: Major color (center): RHS 145B (yellow green). Margins: RHS 138A (yellowish green).

*Color, mature leaf*.—Upper surface: Major color (center): RHS 64B (purplish red). Secondary color (around center): RHS 187A (dark red). Margins: RHS 140A (yellowish green). Base: RHS 149D (yellow green). Lobes (center): RHS 64B (purplish red). Lobes (around center): RHS 187A (dark red). Lobes (margin): RHS 140A (yellowish green). Lower surface: Major color (center): RHS 157A (pale yellow green). Secondary color (around center): RHS N186C (purplish grey). Margins: RHS 138A (yellowish green).

*Petiole length*.—Approximately 2.5 cm.

*Petiole diameter*.—0.25-0.3 cm.

*Petiole color*.—RHS 145B (light yellow green).

*Petiole texture*.—Smooth, no pubescence.

Flowers and seeds: Flowers and seeds have not been observed during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (Bunyaviridae) has also been observed in plants confined in greenhouses with mixed crops (peppers) infected with Western flower thrips (*Frankliniella occidentalis*). The most common pathogen of this species in the U.S. is downy mildew (*Perononspora lamii*). This pathogen has been observed in stock materials grown closely together in cooler growing seasons.

Comparison with Known Cultivars

When compared to the *Coleus* cultivar 'UF16-45-18' (not patented, commercial name of the cultivar is Stained Glass-works® Crown Jewel, owned by Dümmen Group B.V., Netherlands), the new *Coleus* cultivar 'UF20-103-6' has a distinct center-leaf coloration of purplish red surrounded by dark red on the upper surface of mature leaves. In contrast, 'UF16-45-18' has a mostly dark-red leaf coloration with no distinct center-leaf coloration on the upper surface of mature leaves.

What is claimed is:

1. A new and distinct *Coleus scutellarioides* plant named 'UF20-103-6' as shown and described herein.

* * * * *